(12) United States Patent
Hamm et al.

(10) Patent No.: US 12,263,314 B2
(45) Date of Patent: Apr. 1, 2025

(54) IMAGING CATHETER WITH RADIOPAQUE MARKERS

(71) Applicant: Canon U.S.A., Inc., Melville, NY (US)

(72) Inventors: Mark Alan Hamm, Lynnfield, MA (US); Badr Elmaanaoui, Belmont, MA (US); Albert Harold Dunfee, Byfield, MA (US); Kenneth Cooper Lippencott, Mount Tabor, NY (US); Jeffrey Yutien Chen, Winchester, MA (US)

(73) Assignee: Canon U.S.A., Inc., Melville, NY (US)

( * ) Notice: Subject to any disclaimer, the term of this patent is extended or adjusted under 35 U.S.C. 154(b) by 1176 days.

(21) Appl. No.: 16/817,313

(22) Filed: Mar. 12, 2020

(65) Prior Publication Data
US 2020/0297970 A1 Sep. 24, 2020

Related U.S. Application Data

(60) Provisional application No. 62/821,083, filed on Mar. 20, 2019.

(51) Int. Cl.
*A61B 1/07* (2006.01)
*A61B 1/00* (2006.01)
*A61B 5/00* (2006.01)
*A61M 25/01* (2006.01)

(52) U.S. Cl.
CPC ..... *A61M 25/0108* (2013.01); *A61B 1/00133* (2013.01); *A61B 1/00135* (2013.01); *A61B 1/07* (2013.01); *A61B 5/0073* (2013.01); *A61B 5/0084* (2013.01)

(58) Field of Classification Search
CPC .......... A61M 25/0108; A61B 1/00133; A61B 1/00135; A61B 1/07; A61B 5/0073; A61B 5/0084; A61B 1/00172; A61B 1/00177; A61B 5/02007
See application file for complete search history.

(56) References Cited

U.S. PATENT DOCUMENTS

| 5,253,653 | A |   | 10/1993 | Daigle et al. |
|---|---|---|---|---|
| 5,484,409 | A | * | 1/1996 | Atkinson ............ A61M 25/104 |
|   |   |   |   | 606/191 |
| 6,036,682 | A |   | 3/2000 | Lange et al. |
| 6,636,758 | B2 |   | 10/2003 | Sanchez et al. |
| 7,322,959 | B2 |   | 1/2008 | Warnack et al. |
| 9,802,038 | B2 | * | 10/2017 | Lee ........................ B23K 26/40 |

(Continued)

*Primary Examiner* — Baisakhi Roy
(74) *Attorney, Agent, or Firm* — Canon U.S.A., Inc., IP Division (57) ABSTRACT

A catheter, comprising: a drive cable having cylindrical opening extending from a proximal end to a distal end along a longitudinal axis thereof; an imaging probe having an optical fiber arranged inside the drive cable and a distal optics assembly fixedly attached to the drive cable at the distal end thereof; a first radiopaque marker arranged at a distal end of the drive cable at a position distal and parallel to the distal optics assembly; and a second radiopaque marker arranged at a predetermined distance from the distal end of the drive cable at a position proximal to the distal optics assembly. The second radiopaque marker is arranged concentric or coaxially to the longitudinal axis in a space between the longitudinal axis and an outer surface of the drive cable.

17 Claims, 7 Drawing Sheets

(56) References Cited

U.S. PATENT DOCUMENTS

| | | | |
|---|---|---|---|
| 2010/0125322 A1* | 5/2010 | Fitzgerald | A61F 2/95 623/1.11 |
| 2013/0142487 A1* | 6/2013 | Sasaoka | G02B 6/3822 385/60 |
| 2015/0245882 A1 | 9/2015 | Venkatraghavan et al. | |
| 2015/0335309 A1 | 11/2015 | Stigall et al. | |
| 2017/0333149 A1 | 11/2017 | Stigall et al. | |
| 2018/0250010 A1* | 9/2018 | Furey | A61L 31/16 |
| 2019/0022352 A1 | 1/2019 | Gonzalez et al. | |
| 2019/0099237 A1* | 4/2019 | Booker | A61B 5/0066 |
| 2019/0125318 A1* | 5/2019 | Sarna | A61B 10/02 |
| 2019/0134668 A1* | 5/2019 | Riel | A61B 17/22012 |
| 2019/0255339 A1* | 8/2019 | Lee | A61N 1/37205 |
| 2020/0170745 A1* | 6/2020 | Stigall | A61B 90/39 |
| 2021/0068892 A1* | 3/2021 | Urbanski | A61B 18/1482 |
| 2022/0104786 A1* | 4/2022 | Kunio | A61B 5/318 |

\* cited by examiner

IMAGING CATHETER WITH RADIOPAQUE MARKERS

CROSS-REFERENCE TO RELATED APPLICATIONS

The present application claims priority to U.S. provisional application 62/821,083 filed Mar. 20, 2019, the disclosure of which is incorporated by reference herein in its entirety.

BACKGROUND INFORMATION

Field of Disclosure

The present disclosure relates to medical devices. More particularly, the disclosure exemplifies radio-opaque markers for catheters and the like.

Description of Related Art

An endoscope (also referred as "imaging catheter") is a medical device that has imaging capabilities so as to be able to provide images of internal parts (e.g., blood vessels) of a patient. In a catheter for in-vivo imaging, the use of radiopaque markers for radiographically identifying the location of a patient's surgical site and/or for positioning a catheter at the correct site of a patient's vasculature to be treated is very important. For example, in cardiovascular procedures, doctors may use a guide wire having distal radiopaque markers for accessing, estimating or referencing a patient's anatomy to be treated. In addition, in such procedure, doctors need at least one marker at the extreme distal tip of the catheter sheath to know where the tip of the catheter is located with respect to the guidewire tip and/or the patient's anatomy to be treated. Examples of these techniques include U.S. Pat. Nos. 7,322,959, 6,036,682, 6,636,758, and 5,253,653.

In rotating-core imaging catheters configured to image bodily lumens such as a vessel, the imaging core rotates and translates relative to the sheath. During imaging, the catheter sheath is placed across the stenosis or other site of interest and stays stationary while the internal imaging core rotates and pulls back to create a three-dimensional (3D) representation of the vessel. In this case too, doctors need a marker at the distal tip of the sheath to know where the catheter tip is located with respect to the anatomy of interest. An imaging core tip marker is also required to inform the doctor or clinician where the imaging plane or distal optics is located. Examples of these devices are described in various patent publications including US 20140245882, US 20150335309, and US 20170333149.

In the known art described above, the markers are typically radiopaque markers provided over the outer diameter of the guidewire. Having the markers over the outer diameter of the guidewire causes an increase in the effective diameter of the guidewire, and therefore an increase in the entire profile of the catheter device. However, to be able to provide accurate in-vivo imaging of a patient's most delicate internal parts, it is necessary to minimize the profile (in particular the diameter) of the catheter device.

Therefore, a need remains for improvement in determining where the tip of the catheter is located with respect to the guidewire tip and/or the patient's anatomy.

SUMMARY OF EXEMPLARY EMBODIMENTS

According to at least one embodiment, an improved catheter with radiopaque markers is disclosed. The catheter comprises a rotating imaging core and a non-rotating protective sheath. The rotating imaging core includes: a drive cable having cylindrical opening extending from a proximal end to a distal end along a longitudinal axis thereof; an imaging probe having an electrical conductor and/or an optical fiber arranged inside the drive cable and a distal optics assembly fixedly attached to the drive cable at the distal end thereof; a first radiopaque marker arranged at a distal end of the drive cable at a position close to the distal optics assembly; and a second radiopaque marker arranged at a predetermined distance from the distal end of the drive cable at a position proximal to the distal optics assembly. The second radiopaque marker is arranged concentric or coaxially to the longitudinal axis in a space between the longitudinal axis and an outer surface of the drive cable.

There are a number of advantages associated with the present design and arrangement of radiopaque markers for a thin imaging catheter. By placing markers in the wall or within the inner diameter of the drive cable, the radiopaque markers are still functional markers, but they do not build up the effective diameter of the imaging core, and as such, the present design does not increase the outer diameter and/or profile of the catheter device. It is desirable to maintain a low profile device to facilitate access to smaller vessels and/or more distal lesions within the coronary anatomy. The imaging core markers mentioned in this disclosure are imaging core markers that move with the imaging core during imaging.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

DETAILED DESCRIPTION OF EXEMPLARY EMBODIMENTS

The embodiments disclosed herein describe noble metal (e.g., platinum/iridium) radiopaque markers either in the form of bands, solder, or wire coils, which are carefully arranged in the rotating core of an imaging catheter without building up the profile of the catheter device. In some embodiments, solid gold wire coils or bands may be utilized due to their high radio-opacity, which is needed to facilitate easy viewing even in adverse conditions such as through bone or through deep tissue, e.g., in a very large patient.

According to at least one embodiment of the present disclosure, a catheter includes, among other things, a rotating imaging core and a protective outer sheath. The rotating imaging core includes, a drive cable having an opening extending from a proximal end to a distal end along a longitudinal axis thereof, and an optical probe arranged inside the drive cable. Specifically, inside the drive cable, an optical probe is fixedly attached to an inner surface of the drive cable to be able to rotate together with a rotation or oscillation of the drive cable. The optical probe includes a light guiding element such as one or more optical fibers and a distal optics assembly arranged at the distal end of the drive cable. This novel catheter is characterized in that, among other features, a plurality of radiopaque markers are strategically arranged along the longitudinal direction of the drive cable. A first radiopaque marker is arranged at a distal end of the drive cable at a position distal to the optical probe; and a second radiopaque marker is arranged at a predetermined distance from the distal end of drive cable at a position proximal to the optical probe. Notably, at least the second radiopaque marker is arranged concentric or coaxial to the drive cable in a space between the longitudinal axis and an outer surface of the drive cable. Careful placement allows the utilization of radiopaque marker bands, radiopaque wire coils, radiopaque solder, and combinations thereof, without building up the profile of the catheter device.

Figure 1:
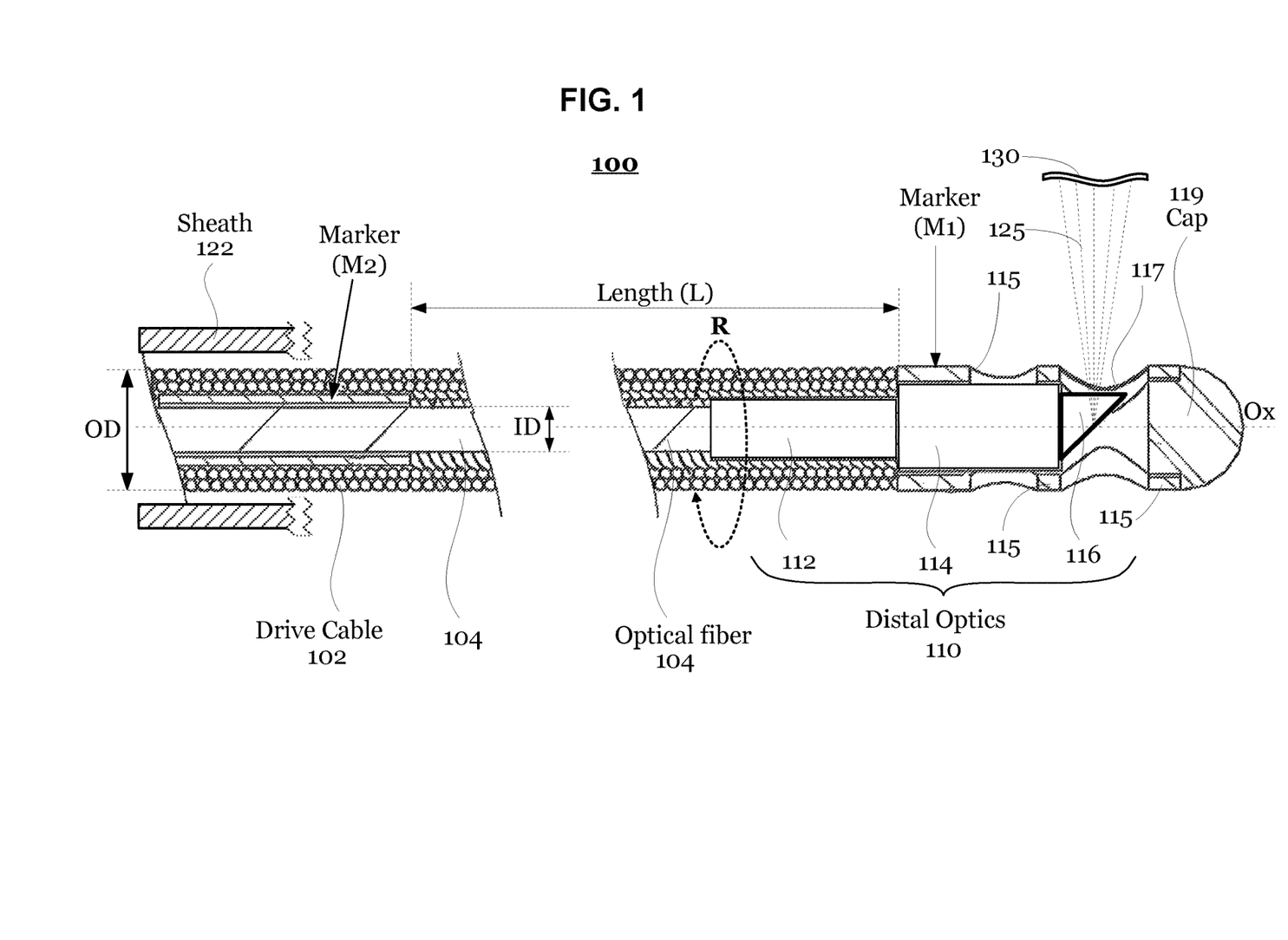
FIG. 1 is a cross sectional view of an exemplary arrangement of radiopaque markers in the imaging core of a catheter, according to a first embodiment.

FIG. 1 is a cross sectional view of an exemplary arrangement of radiopaque markers included in the imaging core of a catheter, according to a first embodiment. In FIG. 1, a multimodality OCT (MMOCT) catheter 100 includes a rotating imaging core arranged inside a protective outer sheath 122. The catheter is coupled at the proximal end thereof with a non-illustrated patient interface unit (PIU). The imaging core includes a drive cable 102 having an inner diameter (ID), an outer diameter (OD), and extending from a proximal end to a distal end along a longitudinal axis Ox. The protective sheath 122 also extends along the longitudinal axis from the proximal end to the distal end. The drive cable 102 is configured to rotate or oscillate in a direction R about longitudinal axis Ox. In addition, the drive cable 102 may also be configured to translate (move) longitudinally parallel to the axis Ox either in a forward or backward direction T while the imaging core scans target sample 130 (e.g., bodily lumen such as a vessel). The torque to rotate and/or translate the drive cable 102 is delivered by a proximal motor located within the PIU (not shown).

Arranged inside the drive cable 102 and fixedly secured thereto is an optical fiber 104; this fiber 104 also extends along the longitudinal axis Ox and is concentric or coaxial thereto. At the distal end, the optical fiber 104 is connected to a distal optics assembly 110. The distal optics assembly 110 includes, for example, a focusing element 112 such as a GRIN lens, a transparent spacer 114 including one or more reflective surfaces, and a dispersive element such as a prism 116. The optical fiber 104 and distal optics assembly 110 is referred herein as an imaging probe, which serves to image a target sample 130. The fiber 104 can be a single mode fiber (SMF) or a double-clad fiber (DCF). A light beam 125 transmitted through the fiber 104 is focused by the distal optics 110 on target sample 13o at about 0.5 to 3.5 mm away from the distal end of the optical probe. Reflected or scattered light is collected by the same distal optics 110 and is delivered to a detection system (not shown) through the fiber 104 in the opposite direction.

The drive cable 102 is attached at its distal end thereof to a metallic tube or can 115. Here, the drive cable 102 may be secured to the metal can 115 by, for example, an adhesive, ultrasonic or laser welding, and the like. This metallic tube or can 115 can be made of radiopaque material, and it includes a side-window 117 in optical alignment with prism 116. This side-window 117 allows the catheter 100 to obtain an image of a target sample 130 using the beam of light 125 in a side-viewing manner. The catheter 100 includes at its distal tip thereof a rounded plug or cap 119 which ensures smooth rotation and translation. The rounded plug or cap 119 may include an adhesive or a metal material, alternatively a metal/polymer material, alternatively stainless steel or other medical grade alloy, which may coaxially fit into the distal portion of the metal tube or can 115; or the cap 119 may be secured to the metal can 115 by adhesive, welding, pressure fitting, and the like.

In order to provide identifying location of a patient's surgical site and/or for providing positioning information, the catheter 100 includes a plurality of radiopaque markers arranged within the diameter of the imaging core. In FIG. 1, a first marker (M1) is an imaging core tip marker which serves to denote the location of the imaging plane. This first marker M1 is built-in within the outer surface of the metal tube or can 115 which protects the distal optics assembly 110. Alternatively, the first marker itself may function as the distal housing (the first marker may replace the metal can 115), which protects the distal optics, and as such, the marker M1 does not build-up the profile of the catheter.

Typical sizes for a catheter of approximately 3 French (3 F) profile, or about 1 millimeter in outer diameter may be used. Markers used in coronary catheter applications range in length from about 1 millimeter to about 2 millimeters (mm), but preferably 1 mm to 1.50 mm in length. In one embodiment, a 3 F catheter utilizes markers that are between 0.50 mm to about 0.75 mm in outer diameter. On the imaging core, marker diameters range from about 0.25 mm to about 0.50 mm in outer diameter, with a wall thickness range of 0.0015 inches to about 0.0025 inches, but preferably between about 0.0015 to 0.0020 inches wall thickness or wire diameter profile if the marker is made of wounded wire. Since wounded wire markers may utilize rectangular cross-section wire, the wire dimensions are typically about 0.0015 to 0.0025 inches across the radial thickness, and about 0.0015 to 0.0050 inches across the axial thickness. In other words, rectangular dimensions of a wounded wire marker having rectangular cross-section range from about 0.0010 to 0.0025 inches in a first direction and 0.0015 to 0.0050 inches in a second direction, and more preferably about 0.0015 inches radially×0.0025 inches axially.

A second radiopaque marker M2 is arranged at a predetermined distance L from the first marker M1. The distance L is useful for indicating to users a length between the distal optics and the distal edge of the secondary marker. In one embodiment, the length of distance L is about 20 millimeters (mm). In another embodiment, the marker M2 is located at, for example, within 5 cm, within 3 cm, within 2 cm, or within 1 cm of the distal end of the drive cable or from the marker M1.

The second marker M2 is a second imaging core marker placed inside or over the drive cable 102 but over the optical fiber 104 such that it is positioned in the space (gap) between the drive cable wall and the optical fiber. In the case of a marker placed over the outer diameter of the imaging core, the marker resides in the space between the imaging core outer diameter and the catheter sheath inner diameter. In one embodiment, the second radiopaque marker M2 is a band marker made of a tubular piece of material having an outer diameter smaller than the inner diameter of the drive cable and an inner diameter equal to (or slightly larger than) the outer diameter of the optical fiber. To facilitate ease of identification, the second marker M2 can be larger or smaller in length than the first marker M1 (tip marker). Since the marker M2 is arranged at a known (predetermined) distance L from marker M1 and it has known dimensions, the marker M2 can give the user a positive length reference, and can also provide with information for orientation, pull-back direction, optical path length calibration, and/or co-registration of images. Notably, since the second marker M2 fits inside the inner diameter of the drive cable 102, it does not build-up the overall profile of the catheter. In fact, since the first marker M1 is also designed to match the outer diameter of the drive cable, both of these imaging core markers M1 and M2 do not build up the diameter of the device, and this design results in a distinct advantage over conventional designs. Suitable materials for the marker M1 and marker M2 include, but are not limited to, radiopaque noble metals such as platinum, platinum-iridium, gold, palladium, and alloys thereof. Since lengthwise the marker M2 is a different size from marker M1, it can be distinguished from marker M1 via fluoroscopy, which is utilized in the co-registration function, utilizing the markers provided along the length of the catheter core to positively identify the lumen (e.g., vessel) to be co-registered, direction of pull-back, etc.

The description below provides illustrations of various forms and arrangements according to which the marker (M2) can be implemented. The second marker M2 can be made of any radiopaque material capable of providing a reference under any known imaging modality capable of detecting radio-opaque material, for example, fluoroscopy X-ray imaging. To that end, at least the second marker M2 can be made of wound wire, for example, of solid gold or platinum-iridium alloy that can be longer than a solid cylindrical marker band. The use of wound or coiled radiopaque wire can be advantageous over the use of solid cylindrical markers as the coiled wire can provide adequate visibility with improved functionality. Specifically, if a solid cylindrical marker band is made too long to increase visibility under an imaging modality, a large sized cylinder forms a rigid length that could interfere with optimum imaging performance by binding in the sheath when it rotates in a tight radius, which can cause significant non-uniform rotation distortion (NURD). In contrast, when using wound or coiled wire inside the wall of the drive cable, the second marker M2 can be made large and still maintain flexibility. Moreover, when the second marker M2 is embedded within the wall of the drive cable, for example, by using radiopaque solder, the outer diameter of the drive cable can be maintained as its minimum while still improving visibility of the marker.

Figure 2:
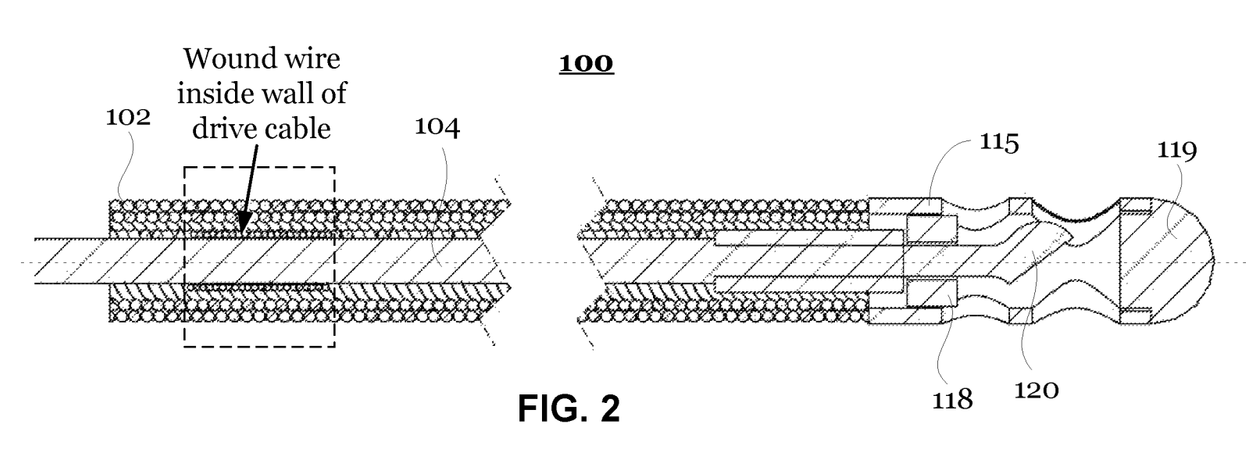
FIG. 2 is a cross sectional view of an exemplary radiopaque marker made of wound wire disposed inside the wall of the drive cable of a catheter.

FIG. 2 is a cross sectional view of an exemplary radiopaque marker M2 made of wound wire disposed inside the wall of the drive cable of a catheter. In FIG. 2, the marker M2 is made of wound or coiled wire in the inner surface of the drive cable 102. In FIG. 2, the rotating core of catheter 100 is similar to that shown in FIG. 1, except that the distal optics assembly 110 includes a ball lens 120 with a reflective surface (instead of prism 116). In addition, in FIG. 2, the distal end of fiber 104 is arranged centrally in the metal can 115 using supports 118.

Figure 3:
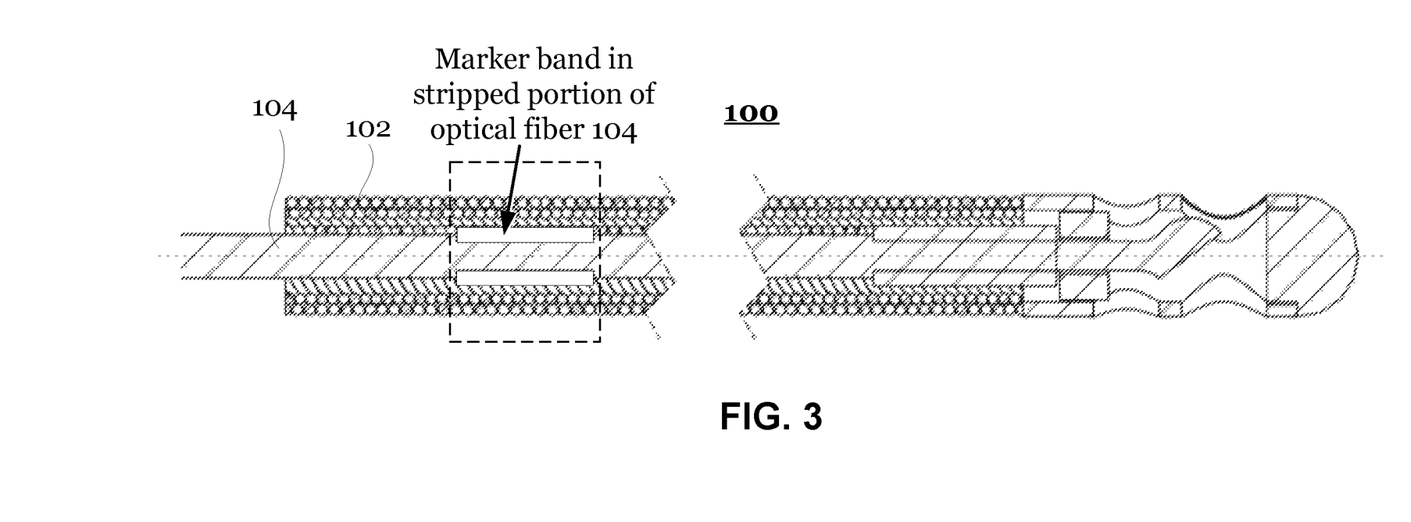
FIG. 3 is a cross sectional view of an exemplary radiopaque marker made of a metallic band disposed in a stripped portion of the optical fiber between the drive cable and the optical fiber of a catheter.

FIG. 3 is a cross sectional view of an exemplary radiopaque marker made of a metallic band disposed in a stripped portion of the optical fiber between the drive cable and the optical fiber of a catheter. In this case, a longitudinal portion of fiber 104 can be stripped of its fiber jacket, cladding, or buffer layer to make space for the marker M2. In FIG. 3, providing a stripped portion of the optical fiber jacket or buffer with a marker band allows for a thicker marker M2, and therefore, provides higher visibility.

Figure 4:
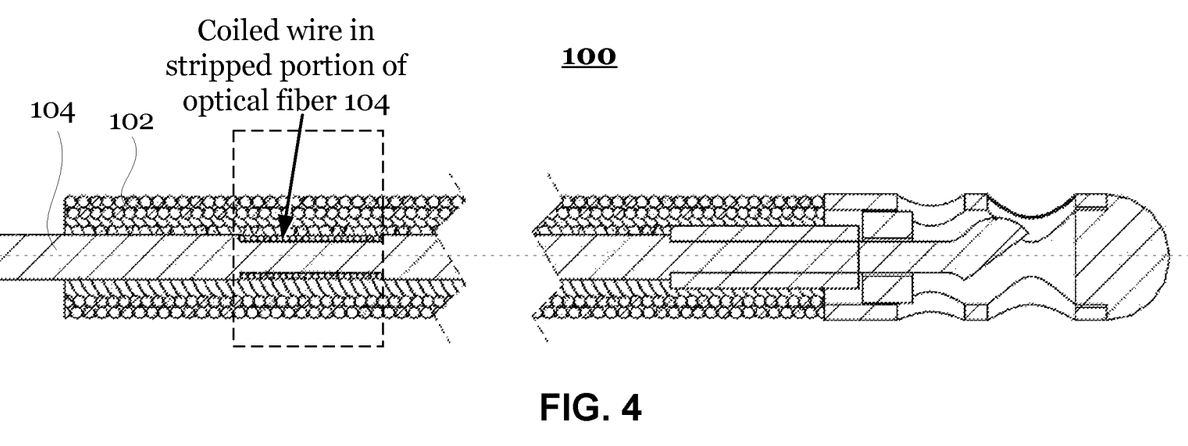
FIG. 4 is a cross sectional view of an exemplary radiopaque marker made of a coiled wire disposed in a stripped portion of the optical fiber between the drive cable and the optical fiber of a catheter.

FIG. 4 is a cross sectional view of an exemplary radiopaque marker made of a coiled wire disposed in a stripped portion of the optical fiber between the drive cable and the optical fiber of a catheter. Similar to FIG. 3, a stripped portion of the optical fiber jacket or buffer is shown with coiled radiopaque R-O wire. In addition, radiopaque solder or radiopaque adhesive material may also be used in the stripped portion of the optical fiber.

As noted above, the markers mentioned in this disclosure, both markers M1 and M2, are imaging core markers that move (rotate and translate) with the imaging core during imaging. Therefore, stripping off the cladding of fiber 104 and arranging therein either a radiopaque band, a coiled radiopaque wire, or radiopaque solder (as shown in FIGS. 3 and 4) does not impair the functionality of the imaging core because the optical and rotational properties of the imaging core remain unchanged.

Figure 5:
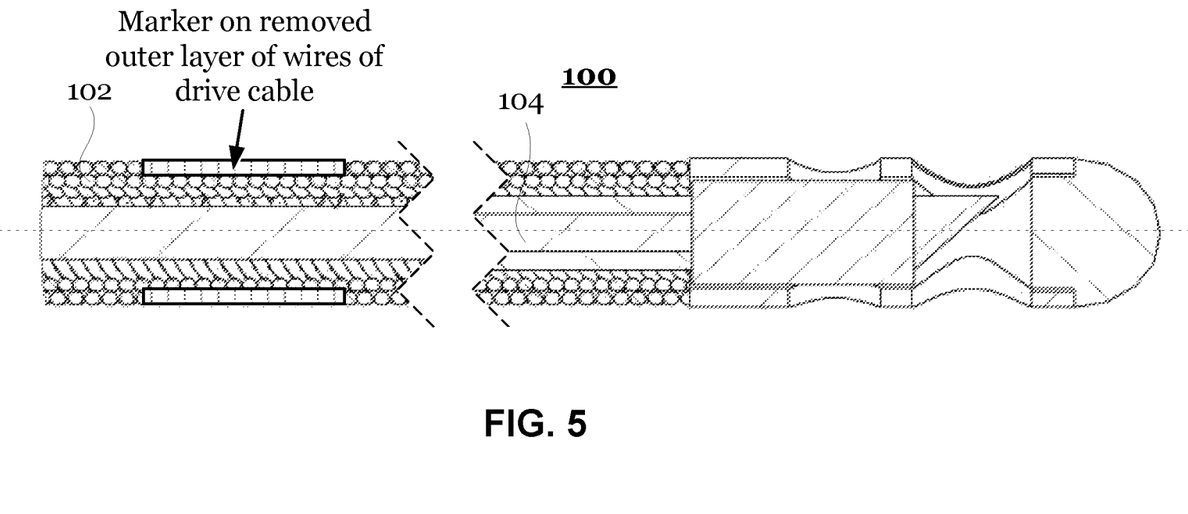
FIG. 5 is a cross sectional view of an exemplary radiopaque marker made of a metallic band or coiled wire disposed in an outer layer of the drive cable of a catheter.

FIG. 5 is a cross sectional view of an exemplary radiopaque marker made of a metallic band or coiled wire disposed in an outer layer of the drive cable of a catheter. As shown in FIG. 5, the drive cable 102 is made of a plurality of layers of wires wound in a helical configuration. In order to provide a marker M2 with higher visibility without increasing the diametric profile of the catheter device, it is advantageous to remove a part (e.g., one layer) of the helically wound wires, and replace the removed layer of wires with radiopaque wires or with a radiopaque band, or to fill the space with radiopaque solder. Removing a portion of the outer layer of wires of the drive cable for a certain length and replacing them with a marker band or platinum wire with a rectangular cross-section allows for a large, highly visible marker M2. The rectangular cross-section wires, when wound next to each other, more accurately simulate a solid, cylindrical marker band, and would maintain flexibility of the imaging core, which is important if the marker M2 is longer that about 1 mm.

Figure 6:
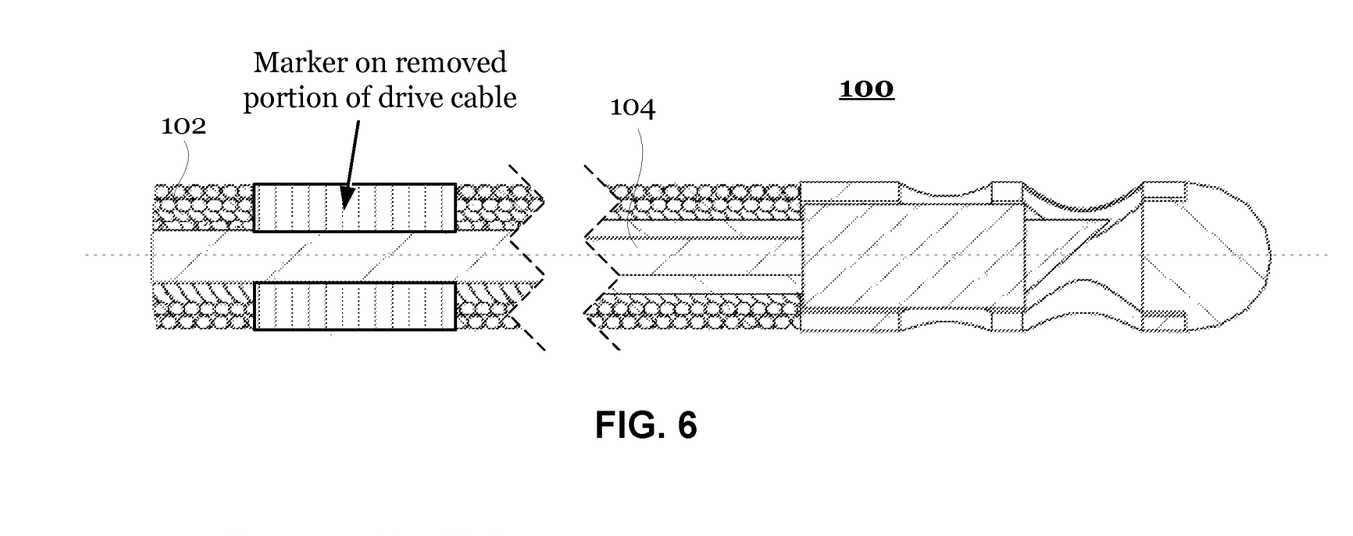
FIG. 6 is a cross sectional view of an exemplary radiopaque marker made of a metallic band or coiled wire disposed in a removed portion of the drive cable of a catheter.

FIG. 6 is a cross sectional view of an exemplary radiopaque marker made of a metallic band or coiled wire disposed in a removed portion of the drive cable of a catheter. Similar to FIG. 5, it is also possible to replace one or more portions of the drive cable 102 with a radiopaque cylindrical band. To maintain flexibility of the catheter, the length of the radiopaque cylindrical band can be limited to less than a few millimeters. In this case too, the marker M2 can include wound radiopaque wires having a rectangular cross-section.

Figure 7:
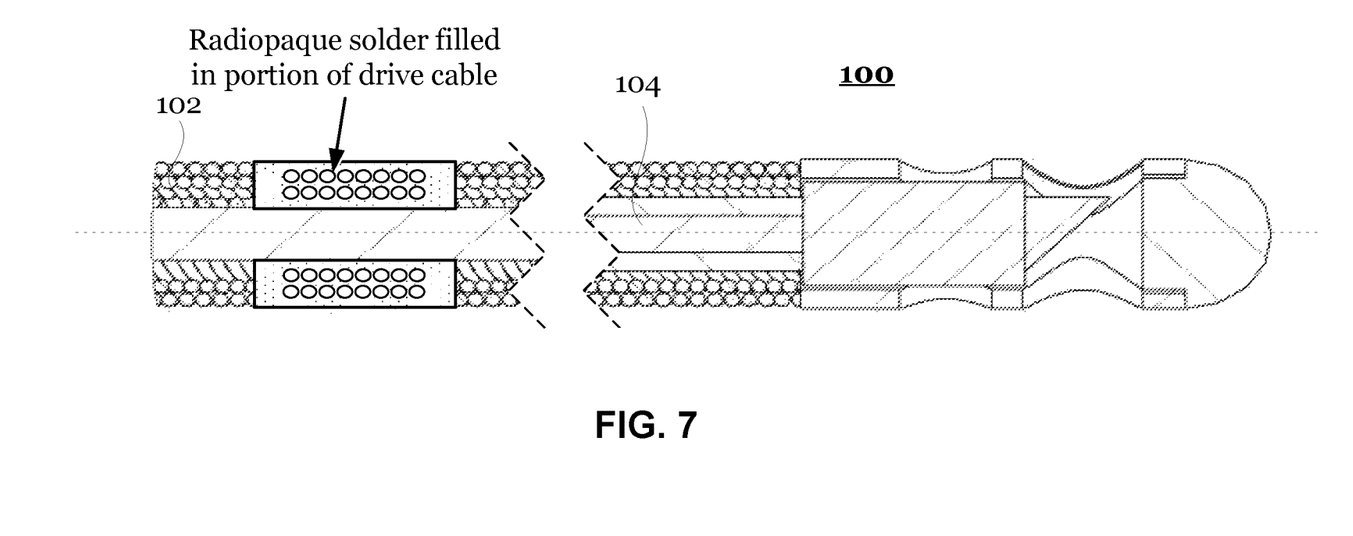
FIG. 7 is a cross sectional view of an exemplary radiopaque marker made of a radiopaque solder filled between coiled wires, in a portion, of the drive cable of a catheter.

FIG. 7 is a cross sectional view of an exemplary radiopaque marker made of radiopaque solder filled between coiled wires, in a portion, of the drive cable of a catheter. Filling the spaces between the helically would wires of the drive cable with radiopaque solder can be one of the easier processes to add one or more radiopaque markers M2 to a catheter device. Use of a radiopaque solder to flow through the space between the wires in the drive cable 102 and the fiber 104, filling all of it can provide a highly visible marker.

Figure 8:
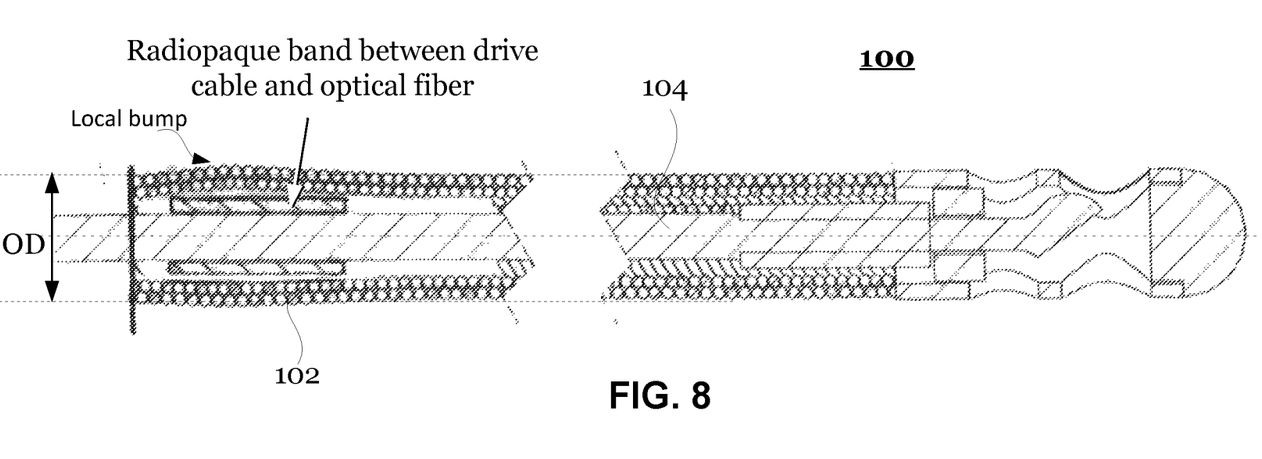
FIG. 8 is a cross sectional view of an exemplary radiopaque marker made of a metallic band or coiled wire disposed between the drive cable and the optical fiber of a catheter.

FIG. 8 is a cross sectional view of an exemplary radiopaque marker made of a metallic band or coiled wire disposed between the drive cable and the optical fiber of a catheter. In FIG. 8, the marker M2 made of a radiopaque band is positioned inside the drive cable between the inner surface of the drive cable and the optical fiber. In this case, the marker M2 has a larger outer diameter than the inner diameter of the drive cable, so the marker M2 may form a minor bump on drive cable.

Figure 9:
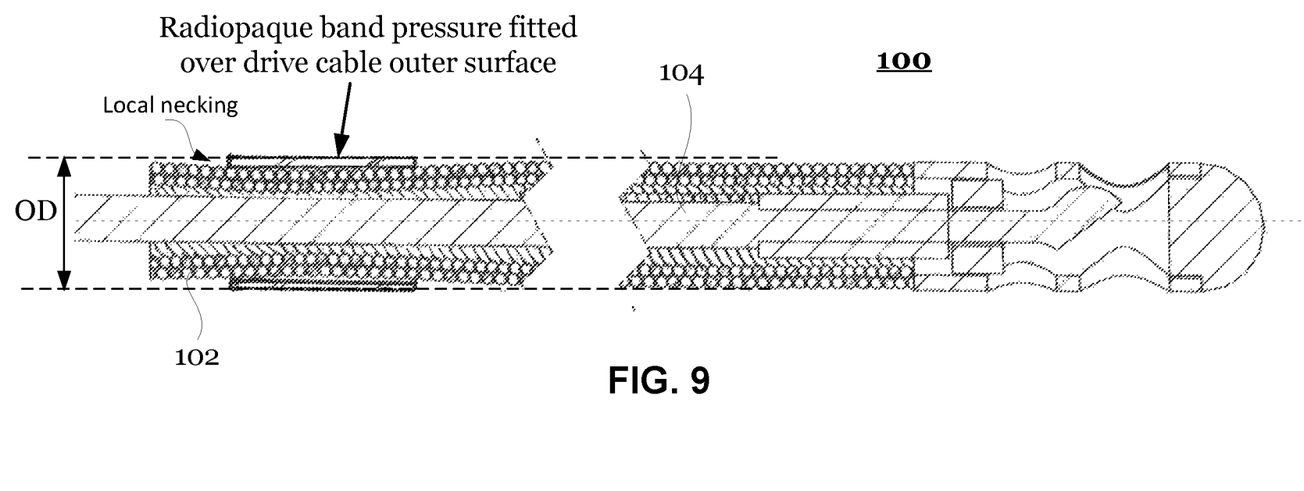
FIG. 9 is a cross sectional view of an exemplary radiopaque marker made of a metallic band or coiled wire pressure fitted over an outer layer of the drive cable of a catheter.

FIG. 9 is a cross sectional view of an exemplary radiopaque marker made of a metallic band or coiled wire pressure fitted over an outer layer of the drive cable of a catheter. Here, the marker M2 is a radiopaque band that fits over the outer diameter of drive cable. In this case, the radiopaque band has a smaller inner diameter than the outer diameter of the drive cable. To assemble the marker M2, pressure fitting the radiopaque band over the drive cable may cause local necking of the drive cable OD. However, the overall outer diameter size of the drive cable can still be maintained substantially unchanged.

Figure 10:
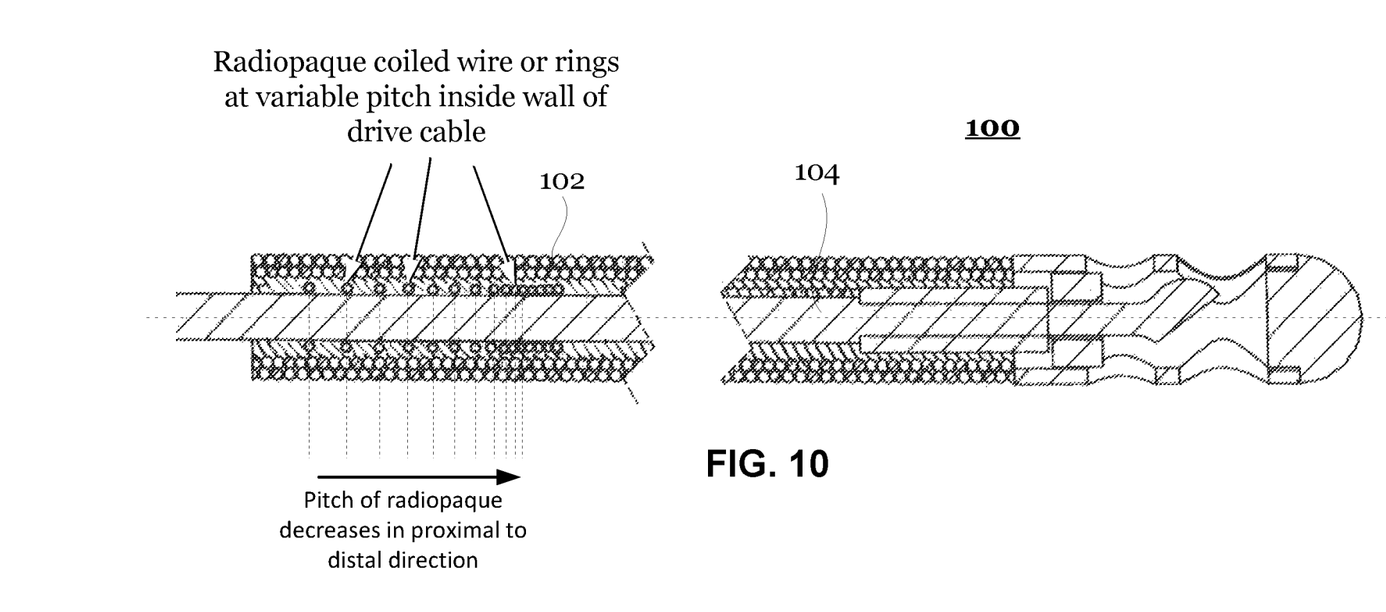
FIG. 10 is a cross sectional view of an exemplary radiopaque marker made of a coiled wire or metallic rings disposed at variable pitch distances inside the wall of the drive cable of a catheter.

FIG. 10 is a cross sectional view of an exemplary radiopaque marker made of a coiled wire or metallic rings disposed at variable pitch distances inside the inner diameter of the drive cable of a catheter. A marker M2 having a variable pitch radiopaque wire coil can advantageously show position and directionality while maintaining flexibility of the fiber and still properly indicating a length between the distal optics and the distal edge of the secondary marker.

In other embodiments of the catheter having radiopaque markers, an atraumatic bullnose tip on the distal end of the radiopaque metal tube or can 115 (distal housing) can be provided. In this case, the ball or cap 119 also functions as an additional radiopaque marker (M3), increasing the visibility of the imaging plane marker, as described below with reference to FIGS. 11 and 12.

Figure 11:
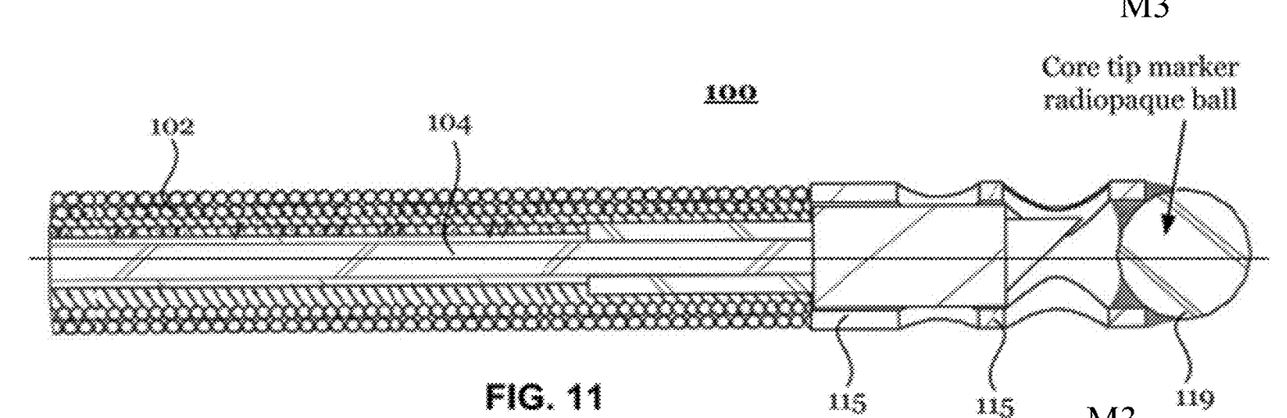
FIG. 11 is a cross sectional view of an exemplary arrangement of radiopaque markers in the imaging core of a catheter, where a core tip marker is a radiopaque ball arranged at the distal tip of the imaging core of a catheter.

FIG. 11 is a cross sectional view of an exemplary arrangement of radiopaque markers in the imaging core of a catheter, where a core tip marker is complemented by the addition of a radiopaque ball arranged at the distal tip of the imaging core of a catheter. As described with reference to FIG. 1, a radiopaque metal tube or can 115 serves as the housing for the distal optics assembly, and also as the first marker M1, which can be arranged at a distal end of the drive cable at a position distal and parallel to the distal optics assembly. For a side-viewing imaging probe, the cap 119 can be replaced with radiopaque ball which can increase the visibility of marker M1 which indicates the position of the imaging plane.

Figure 12:
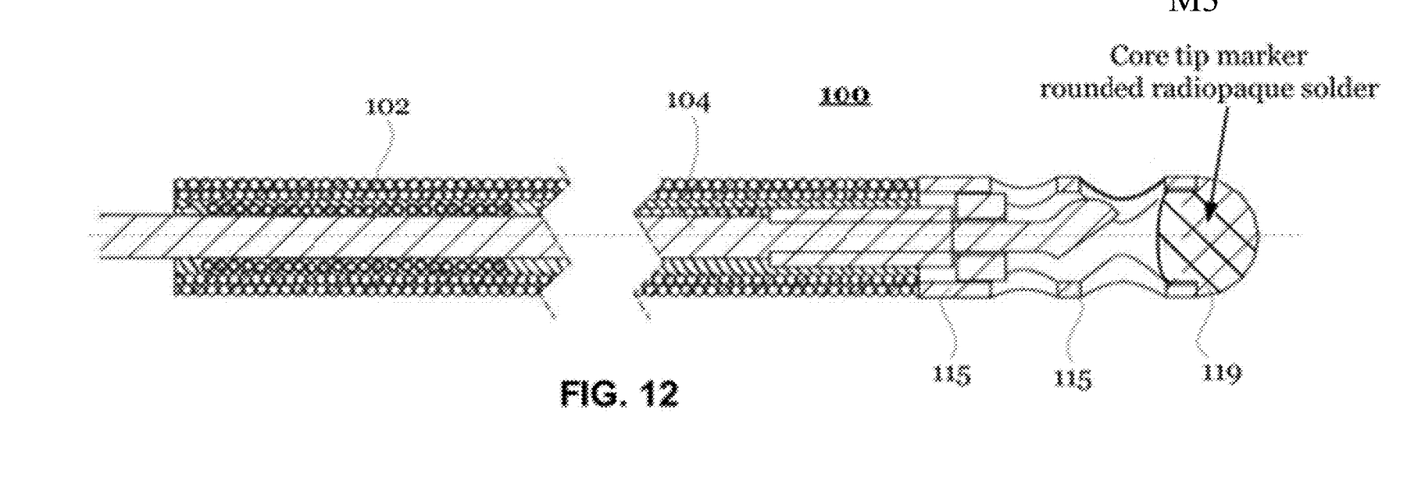
FIG. 12 is a cross sectional view of an exemplary arrangement of radiopaque markers in the imaging core of a catheter, where a core tip marker is complemented by a round tip of radiopaque solder arranged at the distal tip of the imaging core of a catheter.

FIG. 12 is a cross sectional view of an exemplary arrangement of radiopaque markers in the imaging core of a catheter, where a core tip marker is formed of a rounded tip (or an atraumatic bullnose) of radiopaque solder arranged at the distal tip of the imaging core of a catheter, or the radio-opaque solder forming the cap 119 enhances the visibility of the imaging plane provided by the first marker M1. In FIGS. 11 and 12, the radiopaque ball or an atraumatic bullnose not only makes the imaging plane more visible, but it effectively functions as a third radiopaque marker M3 because, for example, the image of the radiopaque ball or traumatic bullnose would show up in the image as a dot (or a rounded edge) at the distal end of the metal can 115. In both cases (FIGS. 11 and 12), it is preferred that this third radiopaque marker M3 be made rotationally symmetric with respect to the longitudinal axis Ox to balance the rotational weight and help avoid resonance and vibrations during rotation which can cause NURD.

There are a number of advantages associated with the present design and arrangement of radiopaque markers for a thin imaging catheter. By placing markers in the wall or within the inner diameter of the drive cable, the radiopaque markers are still functional markers, but they do not build up the effective diameter of the imaging core, and as such, the present design does not increase the outer diameter and/or profile of the catheter device. It is desirable to maintain a low profile device to facilitate access to smaller vessels and/or more distal lesions within the coronary anatomy. The markers mentioned in this disclosure are imaging core markers that move with the imaging core during imaging. In rotating-core imaging catheters, the imaging core rotates and translates relative to the sheath, which is placed across the stenosis or other site of interest. The sheath stays stationary while the internal imaging core rotates and pulls back to create a 3D representation of the vessel.

Radio-opaque (radiopaque) markers come in various shapes and sizes, but most commonly used catheter markers are cylindrical made of platinum-iridium alloy or solid gold bands referred to in the industry as 'marker bands', which are most visible due to their slightly radioactive materials. Other forms of radiopaque markers are filled polymers, dense slugs of metal, coiled wire markers, and radiopaque solder. Coiled wire markers maintain flexibility on the imaging catheters, and for applications where marker bands must be limited in length, coiled wires maintain flexibility of the catheter sheath regardless of length.

Core radiopaque markers in this disclosure do not build up the diameter, but rather are positioned at the tip or in the wall of the drive cable where they do not build up the diameter, or within the inner diameter of the drive cable but over the optical fiber. Some of the embodiments in this disclosure show a second radiopaque marker positioned coaxially or concentrically in a space (gap) between the optical fiber and the internal diameter of the drive cable.

The marker elements described herein are intended to be visualized via fluoroscopy, therefore these markers are preferably made of radio-opaque material, using materials such as platinum, platinum-iridium, gold, tantalum, tungsten, etc., and alloys thereof, which are either very dense or slightly radioactive.

All of the markers described in the present disclosure are rotationally symmetrical markers. Rotationally symmetrical markers are mostly preferred to operate within limited diameters or obstructive luminal spaces, but also beneficial for high speed rotating devices, where balance and rotational symmetry help avoid resonance and vibration which can cause NURD.

Definitions

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. A catheter, comprising:
a drive cable having a cylindrical opening extending from a proximal end to a distal end along a longitudinal axis thereof;
an imaging probe having an optical fiber and a distal optics assembly, the optical fiber arranged inside the cylindrical opening of the drive cable and the distal optics assembly fixedly attached to an inner surface of the drive cable at the distal end thereof;
a first radiopaque marker arranged at the distal end of the drive cable at a position distal and parallel to the distal optics assembly; and
a second radiopaque marker arranged at a predetermined distance from the distal end of the drive cable at a position proximal to the distal optics assembly,
wherein the second radiopaque marker is a coiled radiopaque wire,
wherein the second radiopaque marker is arranged concentric or coaxially to the longitudinal axis in a space between the longitudinal axis and an outer surface of the drive cable, and
wherein the second radiopaque marker is coiled to the longitudinal axis at a progressively decreasing variable pitch.

2. The catheter according to claim 1, further comprising:
a sheath extending concentrically surrounding the drive cable and also extending along the longitudinal axis from the distal end to the proximal end of the drive cable.

3. The catheter according to claim 1, wherein the first radiopaque marker is arranged at the distal end of the imaging probe close to the distal optics assembly.

4. The catheter according to claim 1, wherein the first radiopaque marker functions as a cylindrical housing for the distal optics assembly of the imaging probe.

5. The catheter according to claim 1, wherein the drive cable comprises a plurality of wires wound in a helical configuration to form a lumen having the opening, and
wherein the second radiopaque marker is arranged inside the outer surface of the drive cable and surrounding the optical fiber of the imaging probe.

6. The catheter according to claim 5, wherein the second radiopaque marker is positioned concentric with the longitudinal axis in a gap between the inner surface of the drive cable and the optical fiber.

7. The catheter according to claim 5, wherein the second radiopaque marker is positioned concentric with the longitudinal axis in a gap formed by removing a portion of the cladding of the optical fiber.

8. The catheter according to claim 5, wherein the second radiopaque marker is arranged inside the outer surface of the drive cable by removing a portion of an outer layer of wires of the drive cable for a certain length and replacing the removed portion of the outer layer of the removed wires with a radiopaque marker band or radiopaque wound wire.

9. The catheter according to claim 1, wherein the second radiopaque marker is arranged concentric with the longitudinal axis between an outer diameter and an inner diameter of the drive cable.

10. The catheter according to claim 1, wherein a fixed spacing between adjacent coils progressively decreases in a longitudinal direction from the proximal end to the distal end of the second radiopaque marker.

11. The catheter according to claim 1, further comprising:
a radiopaque ball arranged at the distal end of the catheter,
wherein, in order from the distal end to the proximal end, the catheter includes the radiopaque ball, the first radiopaque marker housing the distal optics assembly thereinside, and the drive cable including the second radiopaque marker.

12. The catheter according to claim 1, further comprising:
a rounded tip arranged at the distal end of the catheter,
wherein the rounded tip is made of radiopaque solder, and
wherein, in order from the distal end to the proximal end, the catheter includes the radiopaque solder, the first radiopaque marker housing the distal optics assembly thereinside, and the drive cable including the second radiopaque marker.

13. The catheter according to claim 1, further comprising:
a third radiopaque marker arranged at the distal end of the catheter at a position distal from the distal optics assembly,
wherein the third radiopaque marker is arranged distal to the first radiopaque marker so as to intersect the longitudinal axis, and
wherein, in order from the distal end to the proximal end, the catheter includes the third radiopaque marker, the first radiopaque marker housing the distal optics assembly thereinside, and the drive cable including the second radiopaque marker.

14. The catheter according to claim 13, wherein the first radiopaque marker and the second radiopaque marker and the third radiopaque marker are symmetric with respect to the longitudinal axis.

15. The catheter according to claim 1, wherein the first radiopaque marker and the second radiopaque marker are symmetric with respect to the longitudinal axis.

16. The catheter according to claim 1, wherein the second radiopaque marker is made of radiopaque wound wire having a rectangular cross-section or a circular cross-section.

17. A catheter comprising:
a drive cable having a cylindrical opening extending from a proximal end to a distal end along a longitudinal axis thereof;
an imaging probe having an optical fiber and a distal optics assembly, the optical fiber arranged inside the cylindrical opening of the drive cable and the distal optics assembly fixedly attached to an inner surface of the drive cable at the distal end thereof;
a first radiopaque marker arranged at the distal end of the drive cable at a position distal and parallel to the distal optics assembly; and
a second radiopaque marker arranged at a predetermined distance from the distal end of the drive cable at a position proximal to the distal optics assembly,
wherein the second radiopaque marker is arranged concentric or coaxially to the longitudinal axis in a space between the longitudinal axis and an outer surface of the drive cable, and
wherein the second radiopaque marker is a cylindrical band formed between the inner diameter of the drive cable and the optical fiber, the cylindrical band having an outer diameter larger than the inner diameter of the drive cable, such that the second marker forms a local bump on the drive cable.

* * * * *